(12) United States Patent
Kuan

(10) Patent No.: US 11,369,563 B2
(45) Date of Patent: Jun. 28, 2022

(54) LOW IRRITATION SKINCARE COSMETIC COMPOSITION

(71) Applicant: ONE PLUS TWO ASSOCIATED CO., LTD., Taipei (TW)

(72) Inventor: Che-Hui Kuan, Taipei (TW)

(73) Assignee: ONE PLUS TWO ASSOCIATED CO., LTD., Taipei (TW)

( * ) Notice: Subject to any disclaimer, the term of this patent is extended or adjusted under 35 U.S.C. 154(b) by 80 days.

(21) Appl. No.: 16/726,807

(22) Filed: Dec. 24, 2019

(65) Prior Publication Data

US 2021/0186858 A1    Jun. 24, 2021

(51) Int. Cl.
| | |
|---|---|
| *A61K 36/00* | (2006.01) |
| *A61K 8/9794* | (2017.01) |
| *A61K 8/9789* | (2017.01) |
| *A61K 8/34* | (2006.01) |
| *A61K 8/73* | (2006.01) |
| *A61K 8/86* | (2006.01) |
| *A61Q 19/00* | (2006.01) |
| *A61K 8/36* | (2006.01) |
| *A61K 8/67* | (2006.01) |

(52) U.S. Cl.
CPC ........... *A61K 8/9794* (2017.08); *A61K 8/345* (2013.01); *A61K 8/361* (2013.01); *A61K 8/678* (2013.01); *A61K 8/735* (2013.01); *A61K 8/86* (2013.01); *A61K 8/9789* (2017.08); *A61Q 19/005* (2013.01); *A61K 2800/30* (2013.01); *A61K 2800/5922* (2013.01); *A61K 2800/75* (2013.01)

(58) Field of Classification Search
CPC ...................................................... A61Q 19/00
See application file for complete search history.

(56) References Cited

U.S. PATENT DOCUMENTS

| | | | | |
|---|---|---|---|---|
| 6,416,769 | B1 * | 7/2002 | Vromen | A61K 8/66 424/401 |
| 9,867,774 | B1 * | 1/2018 | Hakim | A61K 8/19 |
| 2008/0107679 | A1 * | 5/2008 | Dilallo | A61K 36/04 424/195.17 |

FOREIGN PATENT DOCUMENTS

CN              103520039 A   *   1/2014

* cited by examiner

*Primary Examiner* — Qiuwen Mi

(74) *Attorney, Agent, or Firm* — CKC & Partners Co., LLC

(57) ABSTRACT

The present invention provides a low irritation skincare cosmetic composition, which includes 0.00004% to 0.0005% of an *Aloe barbadensis* extract, 0.000005% to 0.00005% of a *Hypericum perforatum* flower leaf stem extract, 0.007% to 0.1% of a *Butyrospermum parkii* (Shea Butter), 0.009% to 5% of a *Helianthus annuus* seed oil, 0.008% to 0.08% of a *Cocos nucifera* oil, 1% to 15% of a moisturizing agent, and water.

20 Claims, No Drawings

LOW IRRITATION SKINCARE COSMETIC COMPOSITION

BACKGROUND

Field of Invention

The present invention relates to a cosmetic composition for skincare. More particularly, the present invention relates to a cosmetic composition for low irritation skincare based on a specific ingredient mixture.

Description of Related Art

There are thousands of skin formulations available to consumers. Further, there are a myriad of different skin types among the population. Such skin types range from normal skin, dry skin, oily skin, and combination skin (e.g., normal/dry, normal/oily, dry/oily). For most of babies, their skin must be more sensitive compared to normal adult. Accordingly, many cosmetic compositions may be harmful or irritating for their skin types.

DETAILED DESCRIPTION

The present disclosure is therefore to provide a low-irritation skincare cosmetic composition for human body, especially for babies body. The composition is an excellent texture and has the following advantages: (1) cruelty-free (i.e., no animal test); (2) low-irritating; (3) pigment-free; (4) fragrance-free; and (5) having many kinds of plant extract and plant oil. The term "cruelty-free" used herein means there is no animal test used on the skincare cosmetic product. The term "pigment-free" used herein means there is no pigment used on the skincare cosmetic product, which is based on color of original composition. In light of advantages mentioned above, the skincare cosmetic composition is mild for babies to use.

According to various embodiments of the present disclosure, a skincare cosmetic composition is provided, and the skincare cosmetic composition at least includes an *Aloe barbadensis* extract (CAS No. 85507-69-3), a *Hypericum perforatum* flower leaf stem extract (CAS No. 84082-80-4), a *Butyrospermum parkii* (Shea Butter) (CAS No. 194043-92-0), a *Helianthus annuus* seed oil (CAS No. 8001-21-6), a *Cocos nucifera* oil (CAS No. 8001-21-6), a moisturizing agent, and water.

By way of example and not limitation, in accordance with some embodiments of the present disclosure, the *Aloe barbadensis* extract in the present disclosure is present in the skincare cosmetic composition at a weight percentage ranged from 0.00004% to 0.0005%, such as 0.00004%, 0.000045%, 0.000048%, 0.00005%, 0.0001%, 0.0002%, 0.0003%, 0.0004%, and 0.0005%. In some embodiments of the present disclosure, the *Hypericum perforatum* flower leaf stem extract is present in the skincare cosmetic composition at a weight percentage ranged from 0.000005% to 0.00005%, for example, 0.000005%, 0.000006%, 0.000007%, 0.0000075%, 0.000015%, 0.00002%, 0.000025%, 0.00003%, 0.00004%, or 0.00005%. In some embodiments of the present disclosure, the *Butyrospermum parkii* is present in the skincare cosmetic composition at a weight percentage ranged from 0.007% to 0.1%, such as 0.007%, 0.008%, 0.009%, 0.01%, 0.05%, 0.055%, 0.06%, 0.07%, 0.08%, 0.09%, and 0.1%. In some embodiments of the present disclosure, the *Helianthus annuus* seed oil is present in the skincare cosmetic composition at a weight percentage ranged from 0.009% to 5%, such as for example, 0.009%, 0.009995%, 0.0099%, 1.999%, 2%, 2.5%, 3%, 3.5%, 4%, 4.5%, and 5%. In some embodiments of the present disclosure, the *Cocos nucifera* oil is present in the skincare cosmetic composition at a weight percentage ranged from 0.008% to 0.08% such as 0.008%, 0.009%, 0.0095%, 0.01%, 0.05%, 0.06%, 0.07%, and 0.08%. In some embodiments of the present disclosure, the moisturizing agent is present in the skincare cosmetic composition at a weight percentage ranged from 1% to 15%, such as 1%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11.0%, 11.5%, 12.0%, 12.5%, 13.0%, 13.5%, 14.0%, 14.5%, 15.0%, or the like. However, the aforementioned weight percentage is not limiting, other weight percentage is within the spirit and scope of this disclosure. Aforementioned the *Aloe barbadensis* extract and the *Hypericum perforatum* flower leaf stem extract are belonged to plant extract and obtained from the *Aloe barbadensis* and the *Hypericum perforatum* flower leaf stem, respectively. For example purposes, the *Aloe barbadensis* extract used herein is for repairing effect. Also, the *Aloe barbadensis* extract is very suitable for skin care after sun exposure, and it can increase the skin moisture content, oxygen content, and has a good lubrication and moisturizing effect. It is noted that the *Aloe barbadensis* extract has anti-sensitive purpose because of rich in amino acids, minerals, vitamins (repair cells). In addition, the *Hypericum perforatum* flower leaf stem extract used herein is also good for repairing effect and enhance the appearance of dry or damaged skin by reducing flaking and restoring suppleness.

In accordance with some embodiments of the present disclosure, the skincare cosmetic composition may optionally further include *Calendula officinalis* flower extract (CAS No. 84776-23-8) and *Anthemis nobilis* flower extract (CAS No. 84649-86-5).

By way of example and not limitation, in embodiments of the present disclosure, the *Calendula officinalis* flower extract is present in the skincare cosmetic composition at a weight percentage ranged from 0.000003% to 0.00005%, such as 0.000003%, 0.000004, 0.0000045%, 0.000005%, 0.00001%, 0.000015%, 0.00002%, 0.00003%, 0.00004%, 0.00005%, or the like. In some embodiments of the present disclosure, the *Anthemis nobilis* flower extract is present in the skincare cosmetic composition at a weight percentage ranged from 0.000003% to 0.00005%, such as 0.000003%, 0.000004, 0.0000045%, 0.000005%, 0.00001%, 0.000015%, 0.00002%, 0.00003%, 0.00004%, and 0.00005%. However, the aforementioned weight percentage is not limiting, other weight percentage is within the spirit and scope of this disclosure.

In accordance with some embodiments of the present disclosure, the skincare cosmetic composition may optionally further include *Tilia cordata* flower extract (CAS No. 84929-52-2), *Centaurea cyanus* flower extract (CAS No. 84012-18-0), *Chamomilla recutita* flower extract (CAS No. 84082-60-0), and a combination thereof.

By way of example and not limitation, in some embodiments of the present disclosure, the *Tilia cordata* flower extract is present in the skincare cosmetic composition at a weight percentage ranged from 0.000003% to 0.00005%, such as 0.000003%, 0.000004, 0.0000045%, 0.000005%, 0.00001%, 0.000015%, 0.00002%, 0.00003%, 0.00004%, 0.00005%, or the like. In some embodiments of the present disclosure, the *Centaurea cyanus* flower extract is present in the skincare cosmetic composition at a weight percentage ranged from 0.000003% to 0.00005%, such as 0.000003%, 0.000004, 0.0000045%, 0.000005%, 0.00001%, 0.000015%, 0.00002%, 0.00003%, 0.00004%, 0.00005%, or the like. In some embodiments of the present disclosure, the *Chamomilla recutita* flower extract is present in the skincare cosmetic composition at a weight percentage ranged from 0.000003% to 0.00005%, such as 0.000003%, 0.000004, 0.0000045%, 0.000005%, 0.00001%, 0.000015%, 0.00002%, 0.00003%, 0.00004%, 0.00005%, or the like. However, the aforementioned weight percentage is not limiting, other weight percentage is within the spirit and scope of this disclosure.

In accordance with some embodiments of the present disclosure, the skincare cosmetic composition may optionally further include *Theobroma cacao* seed butter (CAS No. 84929-52-2), *Olea europaea* fruit oil (CAS No. 84929-52-2), *Mauritia flexuosa* fruit oil (CAS No. 84929-52-2), or a combination thereof.

By way of example and not limitation, in some embodiments of the present disclosure, the *Theobroma cacao* seed butter is present in the skincare cosmetic composition at a weight percentage ranged from 0.001% to 0.1%, such as 0.001%, 0.002%, 0.0025%, 0.05%, 0.06%, 0.07%, 0.08%, 0.09%, 0.1%, or the like. In embodiments of the present disclosure, the *Olea europaea* fruit oil is present in the skincare cosmetic composition at a weight percentage ranged from 0.03% to 0.5%. For example, 0.03%, 0.04%, 0.045%, 0.05%, 0.1%, 0.2%, 0.3%, 0.4%, 0.5%, or the like. In embodiments of the present disclosure, the *Mauritia flexuosa* fruit oil is present in the skincare cosmetic composition at a weight percentage ranged from 0.009% to 0.1%. Such as 0.009%, 0.0095%, 0.01%, 0.02%, 0.03%, 0.04%, 0.05%, 0.06%, 0.07%, 0.08%, 0.09%, 0.1%, or the like. However, the aforementioned weight percentage is not limiting, other weight percentage is within the spirit and scope of this disclosure.

In accordance with some embodiments of the present disclosure, the moisturizing agent of the skincare cosmetic composition may optionally further include glycerin, and the glycerin is present in the skincare cosmetic composition at a weight percentage ranged from 8% to 15%, such as 8%, 9%, 10%, 11%, 12%, 13%, 14%, and 15%. However, the aforementioned weight percentage is not limiting, other weight percentage is within the spirit and scope of this disclosure.

In accordance with some embodiments of the present disclosure, the skincare cosmetic composition may optionally further include *Hamamelis virginiana* water. By way of example and not limitation, in some embodiments of the present disclosure, the *Hamamelis virginiana* water is present in the skincare cosmetic composition at a weight percentage ranged from 0.009% to 0.1%, such as 0.009%, 0.0095%, 0.01%, 0.02%, 0.03%, 0.04%, 0.05%, 0.06%, 0.07%, 0.08%, 0.09%, and 0.1%. In examples where the skincare cosmetic composition includes *Hamamelis virginiana* water, the *Helianthus annuus* seed oil is present in the skincare cosmetic composition at a weight percentage ranged from 1% to 3%, for example, 1% 1.5%, 1.9%, 1999%, 2.5%, 3%, or the like. In examples where the skincare cosmetic composition includes *Hamamelis virginiana* water.

In accordance with some embodiments of the present disclosure, moisturizing agent of the skincare cosmetic composition may include propylene glycol, which is present in the skincare cosmetic composition at a weight percentage ranged from 1% to 5%, for example, 1% 2%, 3%, 4%, 5%, or the like. However, the aforementioned weight percentage is not limiting, other weight percentage is within the spirit and scope of this disclosure.

In accordance with some embodiments of the present disclosure, the skincare cosmetic composition may optionally further include tocopherol. In some examples, the tocopherol is present in the skincare cosmetic composition at a weight percentage ranged from 0.000003% to 0.005%, for example, 0.000003%, 0.000004%, 0.000005%, 0.0005%, 0.001%, 0.002%, 0.003%, 0.004%, 0.005%. In yet some examples, the tocopherol is present in the skincare cosmetic composition at a weight percentage ranged from 0.0006% to 0.01%, such as 0.0006%, 0.0007%, 0.0008%, 0.0009%, 0.001%, 0.002%, 0.003%, 0.004%, 0.005%, 0.006%, 0.007%, 0.008%, 0.009%, and 0.01%.

In accordance with some embodiments of the present disclosure, the skincare cosmetic composition may optionally further include *Prunus amygdalus* dulcis oil (CAS No. 8007-69-0), *Camellia japonica* seed oil (CAS No. 223748-13-8), and *Cocos nucifera* oil (CAS No. 8001-31-8).

In some embodiments of the present disclosure, the *Prunus amygdalus* dulcis oil is present in the skincare cosmetic composition at a weight percentage ranged from 0.009% to 0.1%, such as 0.009%, 0.01%, 0.02%, 0.03%, 0.04%, 0.05%, 0.06%, 0.07%, 0.08%, 0.09%, and 0.1%. In some embodiments of the present disclosure, the *Camellia japonica* seed oil is present in the skincare cosmetic composition at a weight percentage ranged from 0.009% to 0.1%, such as 0.009%, 0.01%, 0.02%, 0.03%, 0.04%, 0.05%, 0.06%, 0.07%, 0.08%, 0.09%, and 0.1%. In some embodiments of the present disclosure, the *Cocos nucifera* oil is present in the skincare cosmetic composition at a weight percentage ranged from 0.009% to 0.1%, such as 0.009%, 0.01%, 0.02%, 0.03%, 0.04%, 0.05%, 0.06%, 0.07%, 0.08%, 0.09%, and 0.1%. However, the aforementioned weight percentage is not limiting, other weight percentage is within the spirit and scope of this disclosure.

In accordance with some embodiments of the present disclosure, the skincare cosmetic composition may optionally further include sodium hyaluronate (CAS No. 9067-32-7). In some embodiments of the present disclosure, the sodium hyaluronate is present in the skincare cosmetic composition at a weight percentage ranged from 0.00005% to 0.0005%, such as 0.00005%, 0.00006%, 0.00007%, 0.00008%, 0.00009%, 0.0001%, 0.0002%, 0.0003%, 0.0004%, and 0.0005%. However, the aforementioned weight percentage is not limiting, other weight percentage is within the spirit and scope of this disclosure.

In accordance with some embodiments of the present disclosure, the skincare cosmetic composition may optionally further include stearic acid. In accordance with some embodiments of the present disclosure, the stearic acid is present in the skincare cosmetic composition at a weight percentage ranged from 1% to 4%, for example, 1%, 2%, 2.5%, 2.8%, 3%, and 4%. However, the aforementioned weight percentage is not limiting, other weight percentage is within the spirit and scope of this disclosure.

In accordance with some embodiments of the present disclosure, the skincare cosmetic composition may optionally further include *Theobroma cacao* extract. In some embodiments of the present disclosure, the *Theobroma cacao* extract is present in the skincare cosmetic composition at a weight percentage ranged from 0.001% to 0.01%. For example, 0.001%, 0.002%, 0.0025%, 0.003%, 0.004%, 0.005%, 0.006%, 0.007%, 0.008%, 0.009%, 0.01%, or the like. However, the aforementioned weight percentage is not limiting, other weight percentage is within the spirit and scope of this disclosure.

In accordance with some embodiments of the present disclosure, the skincare cosmetic composition may optionally further include fragrance. In some embodiments of the present disclosure, the fragrance is selected from vanilla, and the fragrance is present in the skincare cosmetic composition at a weight percentage ranged from 0.01% to 0.05%, such as 0.01%, 0.02%, 0.03%, 0.04%, 0.05%, or the like.

In examples, the skincare cosmetic composition may optionally further include PEG-100 stearate (CAS No. 9004-99-3). The PEG-100 stearate is present in the skincare cosmetic composition at a weight percentage ranged from 0.5% to 1.5%, such as 0.5%, 0.6%, 0.65%, 0.7%, 0.75%, 0.8%, 0.9%, 1.0%, 1.1%, 1.2%, 1.3%, 1.4%, 1.5%, or the like. However, the aforementioned weight percentage is not limiting, other weight percentage is within the spirit and scope of this disclosure.

In accordance with some embodiments of the present disclosure, the moisturizing agent of the skincare cosmetic composition may optionally further include glycerin (CAS No. 56-81-5), arginine (CAS No. 74-79-3), caprylyl glycol (CAS No. 1117-86-8), propylene glycol (CAS No. 57-55-6), triethylhexanoin (CAS No. 7360-38-5), or a combination thereof.

By way of example and not limitation, in some embodiments of the present disclosure, the glycerin is present in the skincare cosmetic composition at a weight percentage ranged from 1% to 10%, such as 1%, 1.5%, 2.0%, 3.0%, 4.0%, 5.0%, 6.0%, 7.0%, 8.0%, 9.0%, 9.0, 9.5%, and 10%. In embodiments of the present disclosure, the arginine is present in the skincare cosmetic composition at a weight percentage ranged from 0.13% to 2%, for example, 0.13%, 0.14%, 0.15%, 0.16%, and 0.17%. In embodiments of the present disclosure, the caprylyl glycol is present in the skincare cosmetic composition at a weight percentage ranged from 0.1% to 0.5%, such as 0.1%, 0.15%, 0.2%, 0.3%, 0.4%, and 0.5%. In some embodiments of the present disclosure, the propylene glycol is present in the skincare cosmetic composition at a weight percentage ranged from 0.001% to 5.0%, for example, 0.001%, 0.002%, 0.0025%, 0.005%, 1%, 3%, 3.5%, 4%, 4.5%, and 5%. In some embodiments of the present disclosure, the triethylhexanoin is present in the skincare cosmetic composition at a weight percentage ranged from 1% to 10%, such as 1%, 2%, 5%, 6%, 7%, 8%, 9%, and 10%. However, the aforementioned weight percentage is not limiting, other weight percentage is within the spirit and scope of this disclosure. It is to be appreciated that other moisturizing agents of the skincare cosmetic composition are within the spirit and scope of this disclosure.

As mentioned above, the moisturizing agents are cosmetic preparations used for protecting skin. These functions are normally performed by sebum produced by healthy skin. The moisturizing agents are available as creams, ointments, bath oils, soap substitutes, or the like. The moisturizing agent includes glycerin, which is polyol small molecule. In polyol moisturizing agent, the glycerin is the most frequently used cosmetic ingredient and has significant function to lubricate human body. In addition, as used herein, the arginine function primarily as hair conditioning agents and skin conditioning agents, which makes babies skin conditioning better protecting function.

In accordance with some embodiments of the present disclosure, the skincare cosmetic composition may optionally further include Rosmarinus officinalis water (CAS No. 84604-14-8). By way of example and not limitation, in some embodiments of the present disclosure, the Rosmarinus officinalis water is present in the skincare cosmetic composition at a weight percentage ranged from 0.005% to 0.01%, for example, 0.005%, 0.006%, 0.007%, 0.008%, 0.009%, and 0.01%. However, the aforementioned weight percentage is not limiting, other weight percentage is within the spirit and scope of this disclosure.

As describe above, the Rosmarinus officinalis water is one of plant extract in the skincare cosmetic composition, which has purifying and anti-irritant properties and is rich in calcium, magnesium, iron, manganese, phosphorus, potassium, zinc, and vitamin B1, vitamin B3 and vitamin C. Accordingly, the Rosmarinus officinalis water has nutritious benefit for human body, especially for babies skincare.

In accordance with some embodiments of the present disclosure, the skincare cosmetic composition may optionally further include an emulsifier selected from the group consisting of xanthan gum (CAS No. 85507-69-3), stearic acid (CAS No. 8002-31-1), glyceryl stearate (CAS No. 142-91-6), isopropyl palmitate (CAS No. 8001-21-6), cetearyl alcohol (CAS No. 67762-27-0/8005-44-5), and a combination thereof.

In accordance with some embodiments of the present disclosure, the emulsifier is present in the skincare cosmetic composition at a weight percentage ranged from 5% to 15%, such as 5%, 6%, 7%, 8%, 9%, 10%, 11%, 12%, 13%, 14%, 15%, or the like. However, the aforementioned weight percentage is not limiting, other weight percentage is within the spirit and scope of this disclosure.

By way of example and not limitation, in some embodiments of the present disclosure, the xanthan gum is present in the skincare cosmetic composition at a weight percentage ranged from 0.09% to 0.5%, such as 0.09%, 0.095%, 0.1%, 0.2%, 0.3%, 0.4%, 0.5%, or the like. In some embodiments of the present disclosure, the stearic acid is present in the skincare cosmetic composition at a weight percentage ranged from 1% to 10%, for example, 1%, 2%, 2.5%, 2.8%, 3%, 4%, 5%, 6%, 7%, 8%, 9%, 10%, or the like. In some embodiments of the present disclosure, the glyceryl stearate is present in the skincare cosmetic composition at a weight percentage ranged from 0.5% to 5%, such as 0.5%, 0.6%, 0.7%, 1.5%, 2%, 2.5%, 3%, 4%, 5%, or the like. In some embodiments of the present disclosure, the isopropyl palmitate is present in the skincare cosmetic composition at a weight percentage ranged from 5% to 15%, such as 5%, 6%, 7%, 8%, 9%, 10%, 11%, 12%, 13%, 14%, 15%, or the like. In some embodiments of the present disclosure, the cetearyl alcohol is present in the skincare cosmetic composition at a weight percentage ranged from 0.05% to 3%, such as 0.05%, 0.06%, 0.07%, 0.08%, 0.09%, 0.6%, 1.8%, 2%, 2.5%, 3%, or the like. However, the aforementioned weight percentage is not limiting, other weight percentage is within the spirit and scope of this disclosure.

In accordance with some embodiments of the present disclosure, the skincare cosmetic composition may optionally further include an antiseptic agent selected from the group consisting of chlorphenesin (CAS No. 104-29-0) and phenoxyethanol (CAS No. 122-99-6).

In accordance with some embodiments of the present disclosure, the antiseptic agent is present in the skincare cosmetic composition at a weight percentage ranged from 0.4% to 1%, such as 0.4%, 0.5%, 0.6%, 0.7%, 0.8%, 0.9%, and 1%. However, the aforementioned weight percentage is not limiting, other weight percentage is within the spirit and scope of this disclosure.

EXAMPLES

The following Examples are provided to illustrate certain aspects of the present disclosure and to aid those of skill in the art in practicing this disclosure. These Examples are in no way to be considered to limit the scope of the disclosure in any manner.

EXAMPLE 1: The ingredients of Example 1 are illustrated in Table 1 below.

TABLE 1

| | Ingredients INCI/Chemical Names present in the raw material | CAS No. | Parts by weight |
|---|---|---|---|
| 1. | Purified Water | 7732-18-5 | 66.9049 |
| 2. | Glycerin | 56-81-5 | 9 |
| 3. | Chlorphenesin | 104-29-0 | 0.26 |
| 4. | Xanthan Gum | 11138-66-2 | 0.1 |
| 5. | *Aloe Barbadensis* Extract | 85507-69-3 | 0.0001 |
| 6. | Propylene Glycol | 57-55-6 | 0.005 |
| 7. | Water | 7732-18-5 | 0.004935 |
| 8. | *Hypericum Perforatum* Flower/Leaf/Stem Extract | 84082-80-4 | 0.000015 |
| 9. | *Calendula Officinalis* Flower Extract | 84776-23-8 | 0.00001 |
| 10. | *Anthemis Nobilis* Flower Extract | 84649-86-5 | 0.00001 |
| 11. | *Tilia Cordata* Flower Extract | 84929-52-2 | 0.00001 |
| 12. | *Centaurea Cyanus* Flower Extract | 84012-18-0 | 0.00001 |
| 13. | *Chamomilla Recutita* (Matricaria) Flower Extract | 84082-60-0 | 0.00001 |
| 14. | *Rosmarinus Officinalis* (Rosemary) Water | 84604-14-8 | 0.008 |
| 15. | Purified Water | 7732-18-5 | 0.002 |
| 16. | Acrylates/C10-30 Alkyl Acrylate Crosspolymer | — | 0.075 |
| 17. | Stearic acid | 57-11-4 | 5 |
| 18. | Cetearyl Alcohol | 67762-27-0/ 8005-44-5 | 1.8 |
| 19. | *Butyrospermum Parkii* (Shea Butter) | 194043-92-0 | 0.05 |
| 20. | *Theobroma Cacao* Seed Butter | 8002-31-1 | 0.05 |
| 21. | Glyceryl Stearate | 31566-31-1 | 2 |
| 22. | Triethylhexanoin | 7360-38-5 | 2 |
| 23. | Isopropyl Palmitate | 142-91-6 | 8 |
| 24. | *Helianthus Annuus* (Sunflower) Seed Oil | 8001-21-6 | 0.9995 |
| 25. | Tocopherol | 1406-18-4 | 0.0005 |
| 26. | *Olea Europaea* (Olive) Fruit Oil | 8001-25-0 | 0.05 |
| 27. | *Cocos Nucifera* Oil | 8001-31-8 | 0.05 |
| 28. | *Mauritia Flexuosa* Fruit Oil | 394239-67-9 | 0.01 |
| 29. | Arginine | 74-79-3 | 0.15 |
| 30. | Phenoxyethanol | 122-99-6 | 0.28 |
| 31. | Caprylyl Glycol | 1117-86-8 | 0.2 |
| 32. | Propylene Glycol | 57-55-6 | 1 |
| | Total | | 100 |

In Example 1, all the plant extract and the plant oil, such as *Aloe barbadensis* extract, *Rosmarinus officinalis* (rosemary) water, *Hypericum perforatum* flower/leaf/stem extract, *Calendula officinalis* flower extract, *Anthemis nobilis* flower extract, *Tilia cordata* flower extract, *Centaurea cyanus* flower extract, *Chamomilla recutita* (matricaria) flower extract, *Butyrospermum parkii* (shea butter), *Theobroma cacao* seed butter, *Helianthus annuus* (sunflower) seed oil, *Olea europaea* (olive) fruit oil, *Cocos nucifera* oil, *Mauritia flexuosa* fruit oil, or the like, are natural, not artificial, thus which are low-irritating skincare cosmetic composition. What's more is when combining all such ingredients may have enough nutrition to make human body nourishing. In this example, the skincare cosmetic composition further includes the glycerin.

EXAMPLE 2: The ingredients of Example 2 are illustrated in Table 2 below.

TABLE 2

| | Ingredients INCI/Chemical Names present in the raw material | CAS No. | Parts by weight |
|---|---|---|---|
| 1. | Purified Water | 7732-18-5 | 66.9049 |
| 2. | Glycerin | 56-81-5 | 4 |
| 3. | Chlorphenesin | 104-29-0 | 0.26 |
| 4. | Propylene Glycol | 57-55-6 | 3 |
| 5. | Xanthan Gum | 11138-66-2 | 0.1 |
| 6. | *Aloe Barbadensis* Extract | 85507-69-3 | 0.0001 |
| 7. | *Hamamelis Virginiana* (Witch Hazel) Water | 84696-19-5 | 0.0095 |
| 8. | Alcohol | 64-17-5 | 0.0005 |
| 9. | Propylene Glycol | 57-55-6 | 0.005 |
| 10. | Purified Water | 7732-18-5 | 0.004935 |
| 11. | *Hypericum Perforatum* Flower/Leaf/Stem Extract | 84082-80-4 | 0.000015 |
| 12. | *Calendula Officinalis* Flower Extract | 84776-23-8 | 0.00001 |
| 13. | *Anthemis Nobilis* Flower Extract | 84649-86-5 | 0.00001 |
| 14. | *Tilia Cordata* Flower Extract | 84929-52-2 | 0.00001 |
| 15. | *Centaurea Cyanus* Flower Extract | 84012-18-0 | 0.00001 |
| 16. | *Chamomilla Recutita* (Matricaria) Flower Extract | 84082-60-0 | 0.00001 |
| 17. | *Rosmarinus Officinalis* (Rosemary) Water | 84604-14-8 | 0.008 |
| 18. | Purified Water | 7732-18-5 | 0.002 |
| 19. | Acrylates/C10-30 Alkyl Acrylate Crosspolymer | — | 0.09 |
| 20. | Stearic acid | 57-11-4 | 5 |
| 21. | Cetearyl Alcohol | 67762-27-0/ 8005-44-5 | 1.8 |
| 22. | *Butyrospermum Parkii* (Shea Butter) | 194043-92-0 | 0.05 |
| 23. | Glyceryl Stearate | 31566-31-1 | 2 |
| 24. | Isopropyl Palmitate | 142-91-6 | 9 |
| 25. | *Helianthus Annuus* (Sunflower) Seed Oil | 8001-21-6 | 1.999 |
| 26. | Tocopherol | 1406-18-4 | 0.001 |
| 27. | *Olea Europaea* (Olive) Fruit Oil | 8001-25-0 | 0.05 |
| 28. | *Cocos Nucifera* Oil | 8001-31-8 | 0.05 |
| 29. | Arginine | 74-79-3 | 0.15 |
| 30. | Phenoxyethanol | 122-99-6 | 0.28 |
| 31. | Caprylyl Glycol | 1117-86-8 | 0.2 |
| | Total | | 100 |

In Example 2, the *Hamamelis virginiana* water is present in the skincare cosmetic composition at a weight percentage ranged from 0.009% to 0.1%, and the *Helianthus annuus* seed oil is present in the skincare cosmetic composition at a weight percentage ranged from 1% to 3%.

As used herein, the *Hamamelis virginiana* water functions as a skin conditioning agents. Such ingredient enhances the protection appearance after suffering dry or damaged skin and helps to reduce flaking and restores the suppleness of skin. Accordingly, the *Hamamelis virginiana* water acts as soothing function in skincare cosmetic composition disclosed herein. As used herein, the *Helianthus annuus* seed oil is a clear, slightly amber-colored liquid. Such ingredient that acts as lubricants on the skin surface, which gives the skin a soft and smooth appearance and enhances the appearance of dry or damaged skin by reducing flaking and restoring suppleness. In light of mentioned above, the *Helianthus annuus* seed oil slows the loss of water from the skin by forming a barrier on the skin's surface, especially protects babies from damaging and keeps their body moisturizing in skincare cosmetic composition disclosed herein.

EXAMPLE 3: The ingredients of Example 3 are illustrated in Table 3 below.

TABLE 3

| | Ingredients INCI/Chemical Names present in the raw material | CAS No. | Parts by weight |
|---|---|---|---|
| 1. | Purified Water | 7732-18-5 | 86.36987 |
| 2. | Chlorphenesin | 104-29-0 | 0.25 |
| 3. | Glycerin | 56-81-5 | 2 |
| 4. | Xanthan Gum | 11138-66-2 | 0.12 |
| 5. | Acrylates/C10-30 Alkyl Acrylate Crosspolymer | — | 0.225 |
| 6. | *Aloe Barbadensis* Extract | 85507-69-3 | 0.00005 |
| 7. | Propylene Glycol | 57-55-6 | 0.0025 |
| 8. | Water | 7732-18-5 | 0.0024675 |
| 9. | *Hypericum Perforatum* Flower/Leaf/Stem Extract | 84082-80-4 | 0.0000075 |
| 10. | *Calendula Officinalis* Flower Extract | 84776-23-8 | 0.000005 |
| 11. | *Anthemis Nobilis* Flower Extract | 84649-86-5 | 0.000005 |
| 12. | *Tilia Cordata* Flower Extract | 84929-52-2 | 0.000005 |
| 13. | *Centaurea Cyanus* Flower Extract | 84012-18-0 | 0.000005 |
| 14. | *Chamomilla Recutita* (Matricaria) Flower Extract | 84082-60-0 | 0.000005 |
| 15. | Cocoa (*Theobroma Cacao*) Extract | — | 0.0025 |
| 16. | Purified Water | 7732-18-5 | 0.025 |
| 17. | Glycerin | 56-81-5 | 0.0225 |
| 18. | Sodium Hyaluronate | 9067-32-7 | 0.00008 |
| 19. | Stearic acid | 57-11-4 | 2.8 |
| 20. | Cetearyl Alcohol | 67762-27-0/ 8005-44-5 | 0.6 |
| 21. | *Butyrospermum Parkii* (Shea Butter) | 194043-92-0 | 0.01 |
| 22. | Glyceryl Stearate | 123-94-4/ 31566-31-1 | 0.7 |
| 23. | PEG-100 Stearate | 9004-99-3 | 0.7 |
| 24. | Triethylhexanoin | 7360-38-5 | 5 |
| 25. | *Helianthus Annuus* (Sunflower) Seed Oil | 8001-21-6 | 0.009995 |
| 26. | Tocopherol | 1406-18-4 | 0.000005 |
| 27. | *Prunus Amygdalus* Dulcis Oil | 8007-69-0 | 0.01 |
| 28. | *Camellia Japonica* Seed Oil | 223748-13-8 | 0.01 |
| 29. | Cocos Nucifera Oil | 8001-31-8 | 0.01 |
| 30. | Arginine | 74-79-3 | 0.17 |
| 31. | Phenoxyethanol | 122-99-6 | 0.24 |
| 32. | Caprylyl Glycol | 1117-86-8 | 0.2 |
| 33. | Propylene Glycol | 57-55-6 | 0.5 |
| 34. | Fragrance | — | 0.02 |
| | Total | | 100 |

In Example 3, the skincare cosmetic composition includes the *Prunus amygdalus dulcis* oil, the *Camellia japonica* seed oil, and the *Cocos nucifera* oil. As used herein, the *Prunus amygdalus dulcis* oil is a pale, straw-colored or colorless oil obtained from almonds. As used herein, the *Prunus amygdalus* dulcis oil acts as a lubricant on the skin surface, which gives the skin a soft and smooth appearance. As used herein, the *Prunus amygdalus dulcis* oil acts as a moisturizing and anti-inflammatory agent. Such ingredient reduces inflammation and soothes skin and helps to restore the elasticity of skin. Further, the *Prunus amygdalus dulcis* oil may provide nourishing and smoothing effects and can be used for sensitive and dry skin, especially mild for babies skincare. As used herein, the *Cocos nucifera* oil acts as skin-conditioning agent and has similar function described above, such as the function of the *Prunus amygdalus dulcis* oil.

In this example, the skincare cosmetic composition includes the sodium hyaluronate, which is one of the best moisturizing agent and is naturally present in inner of human cornea. As used herein, the sodium hyaluronate enhances the appearance of dry or damaged skin by reducing flaking and restoring suppleness.

In this example, the skincare cosmetic composition includes stearic acid. Such ingredient that helps two substances that normally do not mix to become dissolved or dispersed in one another. Also called an emulsifier. In this example, the stearic acid is present in the skincare cosmetic composition at a weight percentage ranged from 1% to 4%. It is worth mentioned that compared to Example 1 and Example 2, the percentage of weight of the stearic acid in Example 3 is less than Example 1 and Example 2. In view of the above, the stearic acid used herein acts as emulsifier, but not heavy and has refreshing function.

In this example, the skincare cosmetic composition includes the *Theobroma cacao* extract. In this example, the skincare cosmetic composition includes the fragrance such as DC-083089 vanilla.

As previously mentioned, the cosmetic composition disclosed in Examples 1-3 are only exemplary, and it is to be understood that other arrangements of the cosmetic composition exist. For instance, certain components in the exemplary embodiment of Example 1 may be replaced with certain components in the exemplary embodiment of Example 2 to yield a different version of the cosmetic component.

The cosmetic compositions described herein may be cruelty-free such that there is no animal test used to components of the skincare cosmetic composition. Accordingly, the components of the skincare cosmetic compositions may be low-irritating. Various natural plant extract and plant oil described may make human body nutritious and smooth. In addition, the components of the skincare cosmetic compositions may be pigment-free such that all the ingredients in the skincare cosmetic composition disclosed herein are original color, there is no other artificial is added. Further, most of the components of the skincare cosmetic compositions may be fragrance-free such that no irritating function is presence in the skincare cosmetic composition. Specifically, it is a low-irritating skincare cosmetic composition. Such features allow the skincare cosmetic composition and their component to be more readily absorbed into the skin of babies. The cosmetic compositions may be designed so that pigment is not included as a component. Further, exemplary embodiments exist in which fragrance is not included as a component. However, in accordance with other versions, fragrance may be added as a component of the cosmetic composition. In order to create the cosmetic compositions, the various components may be measured out into a cup and then mixed together.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A low irritation skincare cosmetic composition, comprising:
    an *Aloe barbadensis* extract, wherein the *Aloe barbadensis* extract is present in the skincare cosmetic composition at a weight percentage ranged from 0.00004% to 0.0005%;
    a *Hypericum perforatum* flower leaf stem extract, wherein the *Hypericum perforatum* flower leaf stem extract is present in the skincare cosmetic composition at a weight percentage ranged from 0.000005% to 0.00005%;

a *Butyrospermum parkii*, wherein the *Butyrospermum parkii* is present in the skincare cosmetic composition at a weight percentage ranged from 0.007% to 0.1%;

a *Helianthus annuus* seed oil, wherein the *Helianthus annuus* seed oil is present in the skincare cosmetic composition at a weight percentage ranged from 0.009% to 5%;

a *Cocos nucifera* oil, wherein the *Cocos nucifera* oil is present in the skincare cosmetic composition at a weight percentage ranged from 0.008% to 0.08%;

a moisturizing agent, wherein the moisturizing agent is a cream, an ointment, or a soap substitute, and the moisturizing agent is present in the skincare cosmetic composition at a weight percentage ranged from 1% to 15%; and water.

2. The low irritation skincare cosmetic composition of claim 1, further comprising *Calendula officinalis* flower extract and *Anthemis nobilis* flower extract.

3. The low irritation skincare cosmetic composition of claim 2, further comprising *Tilia cordata* flower extract, *Centaurea cyanus* flower extract, or *Chamomilla recutita* flower extract.

4. The low irritation skincare cosmetic composition of claim 3, further comprising *Theobroma cacao* seed butter, *Olea europaea* fruit oil, *Mauritia flexuosa* fruit oil, or a combination thereof.

5. The low irritation skincare cosmetic composition of claim 4, wherein the moisturizing agent comprises glycerin, and the glycerin is present in the skincare cosmetic composition at a weight percentage ranged from 8% to 15%.

6. The low irritation skincare cosmetic composition of claim 1, further comprising *Hamamelis virginiana* water, wherein the *Hamamelis virginiana* water is present in the skincare cosmetic composition at a weight percentage ranged from 0.005% to 0.1%, and the *Helianthus annuus* seed oil is present in the skincare cosmetic composition at a weight percentage ranged from 1% to 3%.

7. The low irritation skincare cosmetic composition of claim 6, wherein the moisturizing agent comprises propylene glycol.

8. The low irritation skincare cosmetic composition of claim 7, further comprising tocopherol, wherein the tocopherol is present in the skincare cosmetic composition at a weight percentage ranged from 0.0006% to 0.01%.

9. The low irritation skincare cosmetic composition of claim 1, further comprising *Prunus amygdalus dulcis* oil, or *Camellia japonica* seed oil.

10. The low irritation skincare cosmetic composition of claim 9, further comprising sodium hyaluronate.

11. The low irritation skincare cosmetic composition of claim 10, further comprising stearic acid, wherein the stearic acid is present in the skincare cosmetic composition at a weight percentage ranged from 1% to 4%.

12. The low irritation skincare cosmetic composition of claim 11, further comprising, *Theobroma cacao* extract.

13. The low irritation skincare cosmetic composition of claim 12, further comprising a fragrance.

14. The low irritation skincare cosmetic composition of claim 1, further comprising *Rosmarinus officinalis* water.

15. The low irritation skincare cosmetic composition of claim 1, wherein the moisturizing agent comprises glycerin, arginine, caprylyl glycol, propylene glycol, triethylhexanoin, or a combination thereof.

16. The low irritation skincare cosmetic composition of claim 1, further comprising an emulsifier selected from the group consisting of xanthan gum, stearic acid, glyceryl stearate, isopropyl palmitate, cetearyl alcohol, and a combination thereof.

17. The low irritation skincare cosmetic composition of claim 16, wherein the emulsifier is present in the skincare cosmetic composition at a weight percentage ranged from 5% to 15%.

18. The low irritation skincare cosmetic composition of claim 1, further comprising PEG-100 stearate.

19. The low irritation skincare cosmetic composition of claim 1, further comprising tocopherol.

20. The low irritation skincare cosmetic composition of claim 1, further comprising chlorphenesin, glycerin, xanthan gum, acrylates/C10-30 alkyl acrylate crosspolymer, propylene glycol, *Calendula officinalis* flower extract, *Anthemis nobilis* flower extract, *Tilia cordata* flower extract, *Centaurea cyanus* flower extract, *Chamomilla recutita* flower extract, cocoa extract, sodium hyaluronate, stearic acid, cetearyl alcohol, glyceryl stearate, PEG-100 stearate, tocopherol, *Prunus amygdalus dulcis* oil, *Camellia japonica* seed oil, arginine, phenoxyethanol, caprylyl glycol, and fragrance.

* * * * *